US010434000B2

(12) United States Patent
Anderson et al.

(10) Patent No.: US 10,434,000 B2
(45) Date of Patent: Oct. 8, 2019

(54) JOINT-SUPPORT DEVICE

(71) Applicant: HotCold Motion Compress LLC, Glen Burnie, MD (US)

(72) Inventors: Clayton Anderson, Glen Burnie, MD (US); Danielle N. Anderson, Glen Burnie, MD (US)

(73) Assignee: HOTCOLD MOTION COMPRESS LLC, Glen Burnie, MD (US)

( * ) Notice: Subject to any disclaimer, the term of this patent is extended or adjusted under 35 U.S.C. 154(b) by 426 days.

(21) Appl. No.: 15/146,420

(22) Filed: May 4, 2016

(65) Prior Publication Data

US 2016/0324676 A1  Nov. 10, 2016

Related U.S. Application Data

(60) Provisional application No. 62/156,390, filed on May 4, 2015.

(51) Int. Cl.
| | |
|---|---|
| *A61F 5/01* | (2006.01) |
| *A61F 5/058* | (2006.01) |
| *A61F 7/02* | (2006.01) |
| *A61F 7/10* | (2006.01) |

(52) U.S. Cl.
CPC .......... *A61F 5/0111* (2013.01); *A61F 5/0585* (2013.01); *A61F 7/02* (2013.01); *A61F 7/10* (2013.01); *A61F 2007/023* (2013.01); *A61F 2007/0228* (2013.01)

(58) Field of Classification Search
CPC .... A61F 5/0111; A61F 5/0113; A61F 5/0585; A61F 2007/0228; A61F 2007/023; A61F 2007/0231
USPC .............................................. 602/27, 65, 66
See application file for complete search history.

(56) References Cited

U.S. PATENT DOCUMENTS

| | | | | |
|---|---|---|---|---|
| 5,445,602 A | * | 8/1995 | Grim ..................... | A61F 5/0111 602/27 |
| 5,520,628 A | * | 5/1996 | Wehr ..................... | A61F 5/0127 128/882 |
| 5,743,867 A | * | 4/1998 | Hickling ................. | A61F 7/02 602/2 |
| 2013/0012855 A1 | * | 1/2013 | Giza ..................... | A61F 5/0111 602/27 |

* cited by examiner

*Primary Examiner* — Kari K Rodriquez
(74) *Attorney, Agent, or Firm* — Steven Scott Lloyd

(57) ABSTRACT

Disclosed herein is an adjustable joint-support apparatus and device for use in treating pain, inflammation, and or other injury to a joint and joint area of a body, and configured for physical and functional flexibility, in that the joint support is flexible and can be worn over clothing. The device is generally suited for support of an ankle joint, a knee joint, a wrist joint, although could also support an elbow, shoulder or hip joint with minimal modifications. In one embodiment, a joint support device/apparatus comprises: one or more of a support member; and at least one securement means configured for providing compression to the joint area of a wearer.

7 Claims, 4 Drawing Sheets

JOINT-SUPPORT DEVICE

CROSS REFERENCE TO RELATED APPLICATIONS

This application claims priority to earlier filed U.S. Provisional patent application No. 62/156,390, filed on May 4, 2015, the contents of which are herein incorporated by reference in their entirety.

BACKGROUND

In response to an ankle injury, rest and ice are typically an integral part of recovery. In a busy lifestyle it's tough to stay stationary often enough, and long enough to thoroughly ice/heat the injured area as prescribed. In many cases, patients are limited to ice/heat treatments when they have the opportunity to remain stationary. Time spent waiting for convenience is essentially missed opportunities for patients to administer ice/heat. Shortened ice/heat rehab sessions also could significantly lengthen a patient's recovery time.

SUMMARY OF THE INVENTION

The present invention was created out of a need to be mobile and not stationery, while administering ice to an injured ankle. An active person who suffers one or both of an ankle and/or Achilles injuries, needs a treatment option that offers versatility while rehabilitating, because remaining in a stationery position without wearing a shoe on the injured foot, isn't always an option. The present invention is a device that is unique in its ability to administer ice and/or heat to the injured area, and to apply compression to the affected area, without restricting motion and mobility of the patient wearing the device. The present invention also performs extremely reliably with or without shoes, such as if the patient wears the device in response to an injury of the ankle or Achilles region.

By offering patients the both options of unrestricted motion and ability to wear footwear, this device drastically expands the patients opportunity to get high quality ice/heat rehabilitation. Thus potentially shortening recovery time. Whether feet up on the couch while watching television, wearing dress shoes in a meeting, or while jumping rope on one leg; you'll never miss a chance for ice/heat rehab.

This device was developed to offer patients suffering from an injury a superior rehabilitation experience by offering the flexibility and versatility. This device is unique in that is offers wearers a new option; the ability to get high quality ice/heat rehabilitation whether at rest or on the go. The device was created not only as an icing/heating tool for ankle/Achilles injury rehabilitation, it's also a new market alternative to the common categories (wraps, stirrups, sleeves). The device was developed to perform at a high level in a variety of use scenarios.

Disclosed herein is an adjustable joint-support apparatus and device for use in treating pain, inflammation, and or other injury to a joint and joint area of a body, and configured for physical and functional flexibility, in that the joint support is flexible and can be worn over clothing. The device is generally suited for support of an ankle joint, a knee joint, a wrist joint, although could also support an elbow, shoulder or hip joint with minimal modifications. In one particular embodiment as an ankle-joint support, a key benefit over presently known support devices is the support does not limit the user's mobility or require the user to forgo standard footwear. According to one embodiment of the present invention, the support is configured with heating and/or cooling means, such as compartments for securing temperature-control members, such as inserts designed to apply heat and/or cool the joint area, or, alternatively, detachable temperature-control members configured to enable the support to emit heat (to heat the joint and surrounding tissue) or absorb heat (to cool the joint area and surrounding tissue). In another embodiment, the joint support is additionally configured with compression means, comprising a compression strap or other wrap for fastening around the exterior of the support when the support is aligned in position over a wearer's joint, so that additional pressure is applied to the joint encased in the support.

Therefore, in one embodiment, the present invention provides a novel adjustable ankle joint support configured to provide resistance to normal joint movement, such as the ankle, but relatively ineffective to hamper or impair normal movement of the foot. In another embodiment, the present invention provides a novel adjustable ankle support that may be worn over stockings and/or clothing, and even permits the use of standard footwear. In yet another embodiment, the present invention provides an adjustable support device adaptable for one or more joints, such as a knee joint; wrist joint; elbow joint; shoulder joint; and hip joint.

In one exemplary embodiment of the present invention, a novel joint support comprises: one or more support members; at least one of a temperature-control member; a first securement means; and a second securement means. In another embodiment the support members are conjoined. In yet another embodiment, the joint support comprises a single support member, or a plurality of support members, depending the joint area to be supported.

In one particular embodiment as a joint support device, the support device is configured to provide a constant, or an adjustable, tension around the ankle of the wearer.

In one embodiment, a joint support device/apparatus comprises: one or more of a support member; and at least one securement means configured for providing compression to the joint area of a wearer.

In another embodiment, a joint support apparatus, comprises: one or more joint support members, one or more securement means; and at least one of a temperature-control means, wherein the temperature control means comprise one or both of a heating element or a cooling element.

In yet another embodiment, a joint support apparatus, comprises: one or more of a support member, the support member configured with a joint facing side and an outward facing side; at least one securement means configured for providing compression to the joint area of a wearer; and a decorative feature affixed to the outward facing surface of a support member.

Also disclosed is a method of treating pain, inflammation, and or other injury to an ankle joint of a patient, comprising: aligning one or more of a support member configured with an joint facing side and an outward facing side on either side of the injured ankle joint; tightening a first securement means by bringing ends together and securing at an appropriate tightness to provide compression against the ankle joint, and wherein the first securement means is connected to the one or more support members via lacing through the support members and secured in an under-weave arrangement between the support members and positioned near the front of the ankle joint; and securing a second securement means around the outer facing side of the support members aligned around the injured joint near the bottom portion of the support members, and wherein the second securement means are secured in an over-weave arrangement to provide appropriate tension around the support members and provide compression again the injured ankle joint.

DETAILED DESCRIPTION OF THE INVENTION

Figure 1:
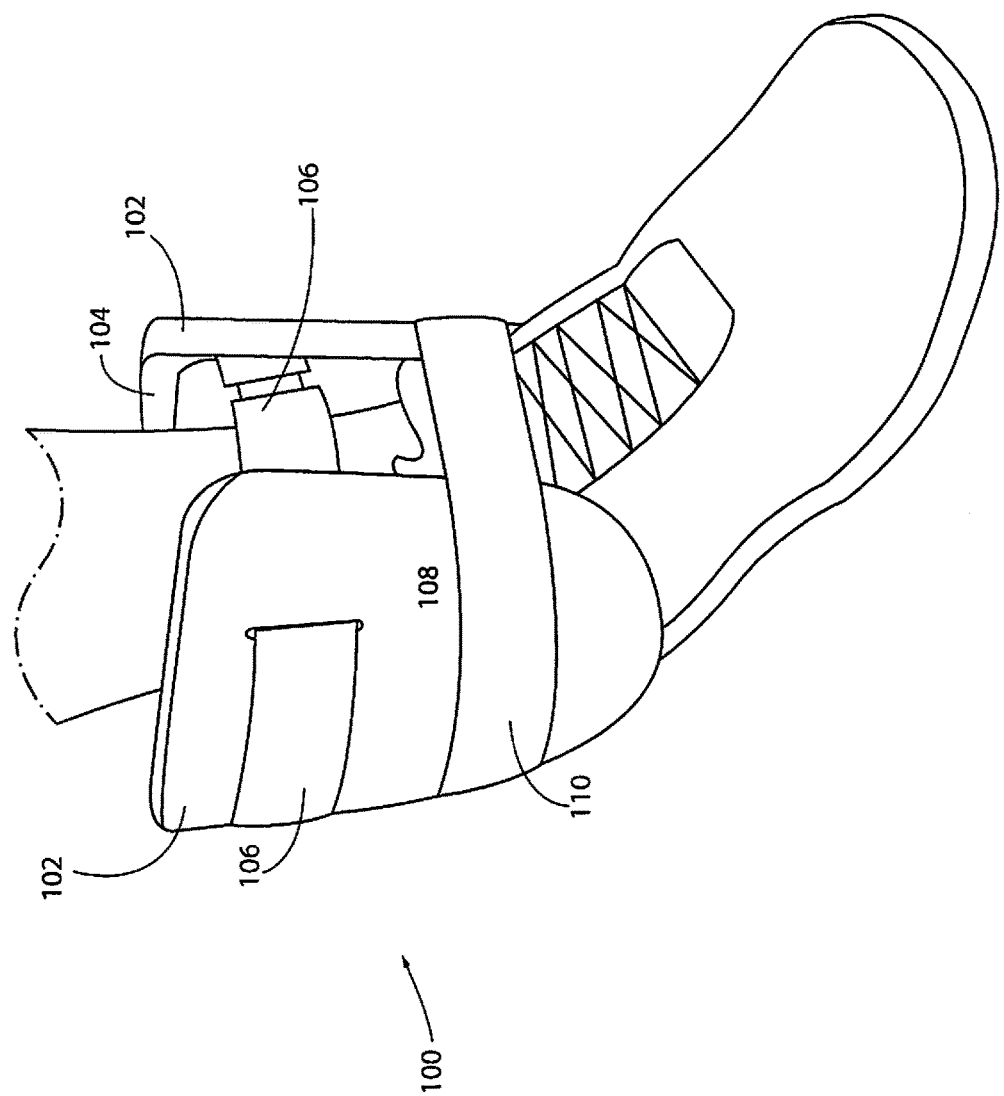
FIG. 1 shows a joint support apparatus (assembled) configured for use as an ankle support, according to one embodiment of the present invention.

Herein, reference is made to the accompanying drawings of the invention, wherein is shown various embodiments of the invention. In the various embodiments shown in the drawings, one or more support members comprise a joint-facing side to abut and cover a joint area. For example, support members are configured to cover and support a region around a joint, such as a fibular side and a tibia side, and/or configured to support an outer joint area and an inner joint area on either side of the ankle. In one embodiment, the support members are held in position around the joint of the wearer by one or more securement means. In another embodiment, support members and securement means are configured to provide compression to the joint area, adjustable depending on the tautness of securement means, when the device is fully assembled on the joint area.

FIG. 1 shows a join support apparatus (assembled) 100 comprising a pair of joint support members 102, contoured in shape to fit over an ankle area of a wearer (shown in the Figure as positioned over the inner and outer area covering the ankle region of the wearer). Support members 102 have a joint facing surface 104. Joint support members 102 are held in position around the joint of a wearer by a first securement means 106 (shown in FIG. 1 as a strap). First securement means 106 is positioned near the top end of the support members and interwoven within the support members 102 via one or more openings 108 positioned on the support members 102 near a top edge. Openings 108 are vertically oriented (up/down) and positioned as a row. The strap 106 is woven/laced through the opening 108, thereby traversing the support member 102 at openings 108 so that a portion of the strap resides on the outward facing side of the support member, and a portion of the strap resides on the inward facing side of the support member. Ends of the first securement means are secured to each other, forming a closure, in an area near the underside of the support members, in what is termed an "under-weave arrangement".

The support members 102 align on either side of the joint, shown in the Figure as fitting around the left side and right side of the ankle joint. In one embodiment, the strap is an elasticized strap, and configured with securement means, such as snaps, buttons, magnetic fasteners, Velcro, ties, or other suitable means of securing the strap at a particular length around the ankle that holds the support members in position. Apparatus 100 is configured with a second securement means 110 (shown in the Figure as a strap wrapped around the outer surface of support members 102). First securement means and second securement means provide compression of the support members on the joint area. Second securement means wrap on the outer side of the support members, in what is termed an "over-weave arrangement", for compression control and ease of assembly and removal. In FIG. 1, second securement means is shown as a strap. In one embodiment, the strap is an elasticized strap, and configured with securement means, such as snaps, buttons, magnetic fasteners, Velcro, ties, or other suitable means of securing the strap around the assembled support members at a tension to provide compression against the joint area.

Figure 2:
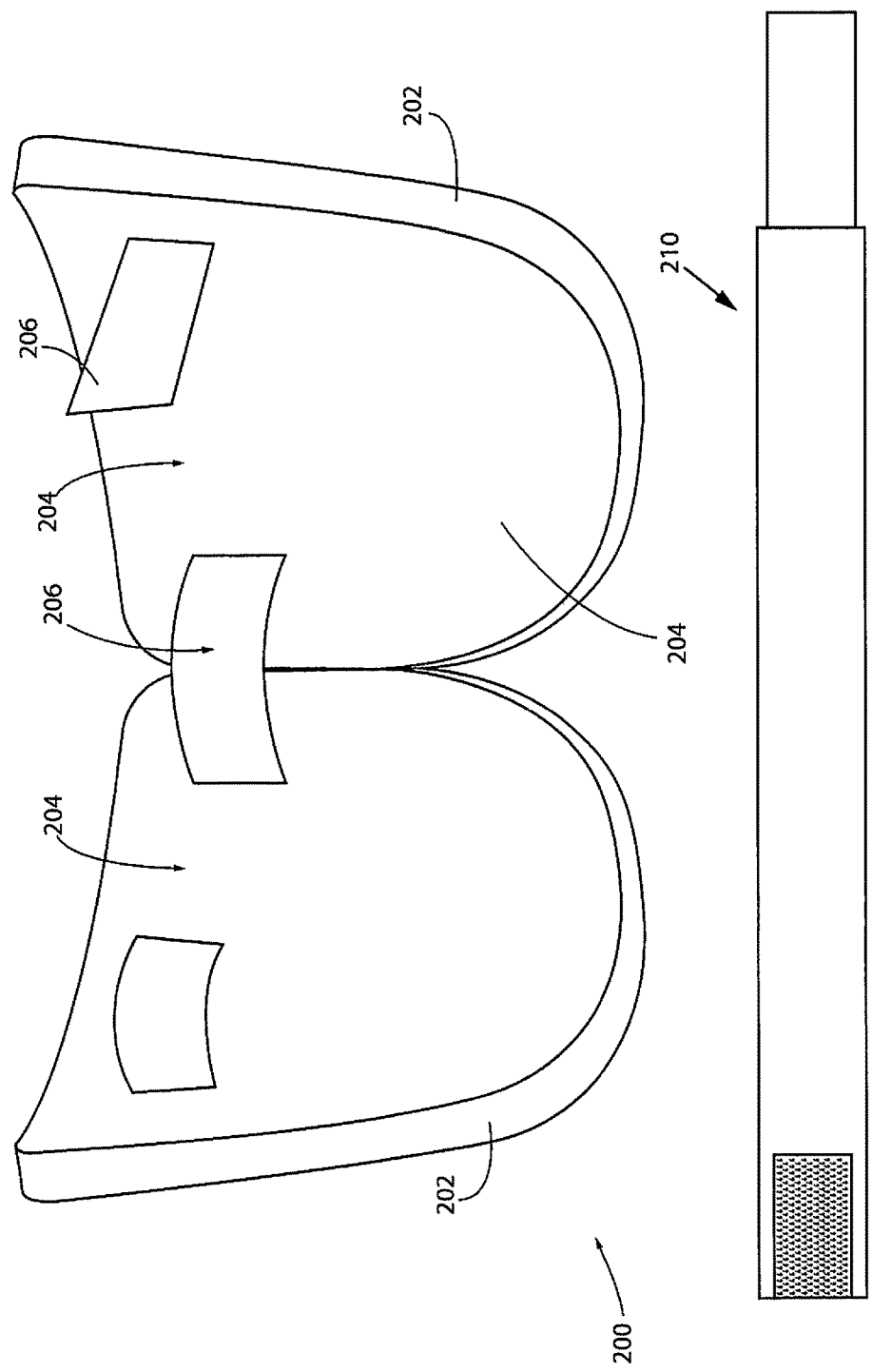
FIG. 2 shows a joint support apparatus (partially unassembled) according to one embodiment of the present invention.

FIG. 2 shows a joint apparatus (unassembled) 200 comprising a pair of support members 202 with a joint facing side 204, wherein the support members 202 are configured with a plurality of openings 208 through which first securement means 206 is interwoven. First securement means 206 is shown in FIG. 2 as a strap. To assemble apparatus 200, support members 202 are aligned on either side of an ankle joint of a wearer, and strap 206 is secured by bringing the ends together and securing the strap at a length the keeps the support members 202 aligned securely at the joint. Also shown in FIG. 2 is second securement means 210, shown in the Figure as a strap configured with Velcro fasteners at either end of the strap.

Figure 3:
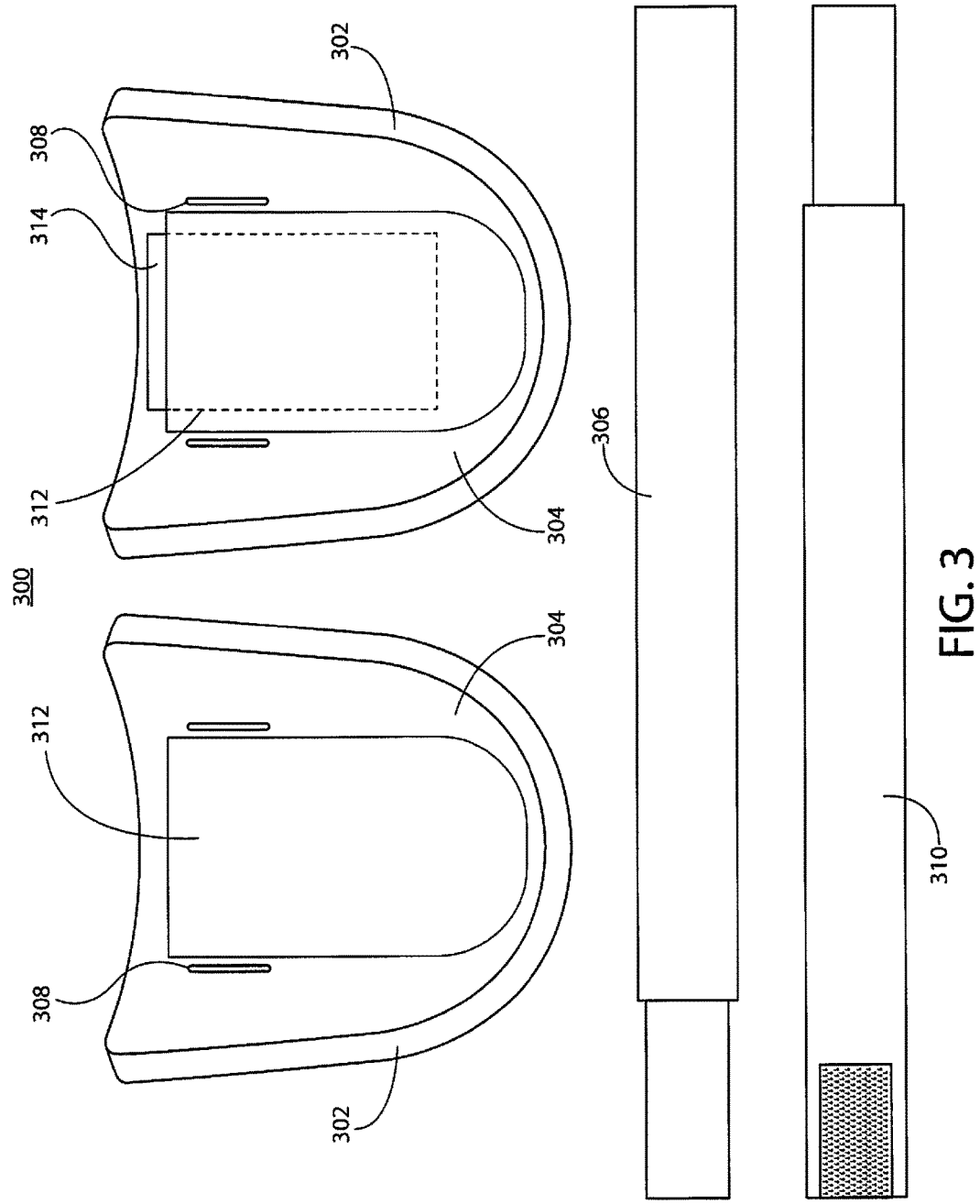
FIG. 3 shows an unassembled joint support apparatus configured with storage compartments for one or more temperature control members, according to one embodiment of the present invention.

Shown in FIG. 3 is a joint apparatus (unassembled) 300 comprising a pair of support members 302 configured with an inner storage compartment 312 on the joint-facing inner surface 304 of support members 302 for storage of a heating or cooling element 314. Also shown on support members 302 are openings 308 for weaving of first securement means 306. Second securement means 310 is also shown.

Figure 4:
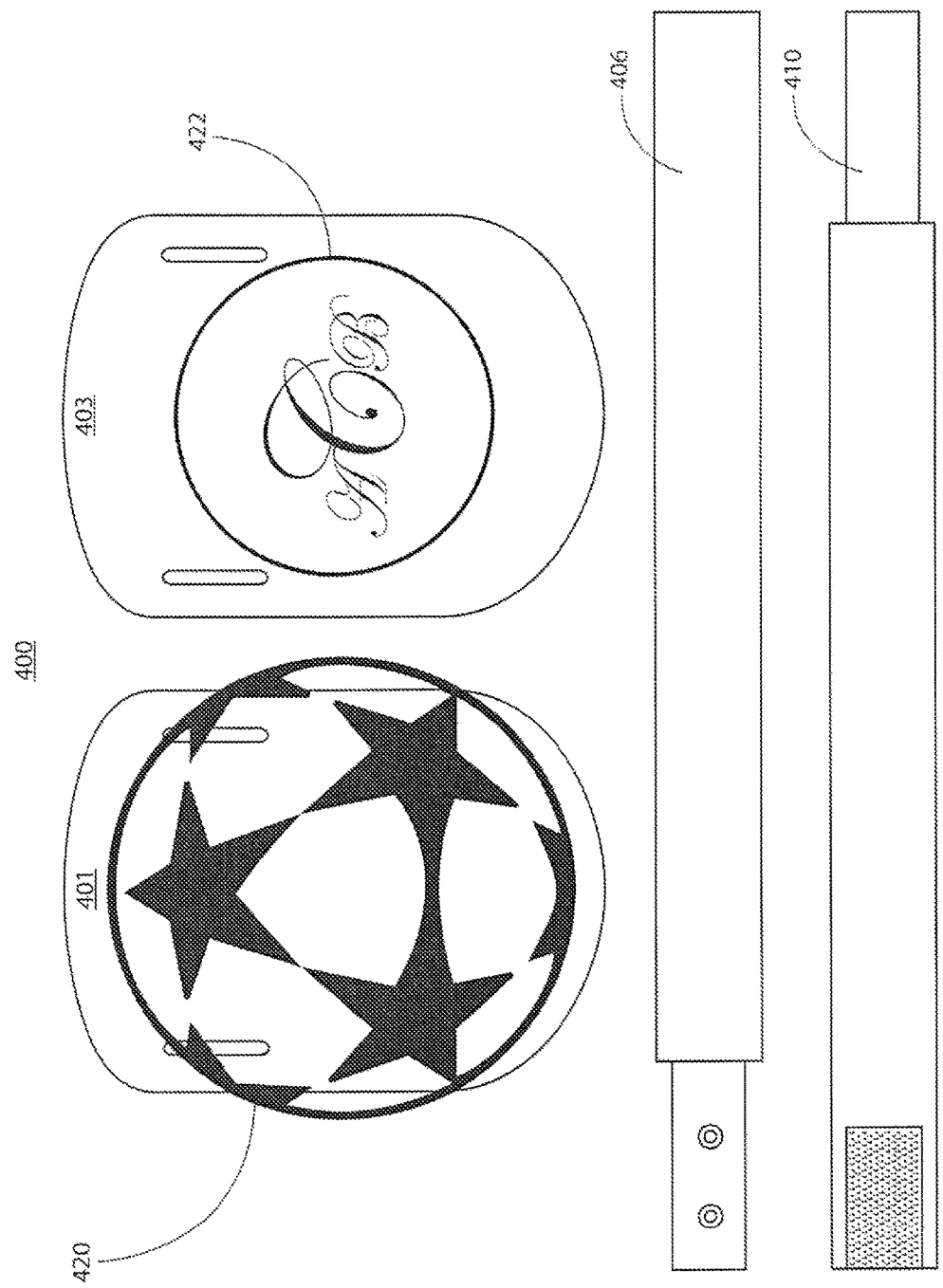
FIG. 4 shows an unassembled joint support apparatus configured with a decorative attachment, according to one embodiment of the present invention.

FIG. 4 shows a joint apparatus (unassembled) 400 comprising a first support member 401 configured with a decorative feature 420 attached to the outer facing surface of support member 401. In one embodiment, decorative feature 420 is shown in the figure as an overlay configured as a soccer ball. In one embodiment, the decorative feature is essentially flat, or may be a 2- or -3 dimensional feature that attached to the outer surface of the support member, or wraps around the support member to which the feature attaches. In one embodiment, a decorative feature may be comprised of natural and/or synthetic materials, such as nylon, plastic, leather, or the like and any combination thereof. Also shown is a support member 403 configured with a decorative feature 422, shown here as a monogram disposed on the surface of the support member 403 on the outward-facing side. Decorative layer may be attached by various attachment means, including but not limited to Velcro, snaps, magnets, tape, glue, adhesives and the like. Decorative layer may also be embossed, engraved, reversibly attached or permanently attached to support member 403. Also shown in FIG. 4 are securement means, comprising straps configured with fastening means, such as snaps shown on strap 406 and Velcro on strap 410.

In one embodiment, the support members are comprised of natural and/or synthetic materials, and may be of one or more layers of materials of varying thickness. In one embodiment, materials may be an oblong piece of one or more of a durable, flexible, impermeable, resilient, natural or synthetic material, such as: chemically-resistant plastics, such as polyethylene or polypropylene, and foams, such as polyurethane foam. In one embodiment, meant to be illustrative and not exhaustive, support members are generally of a size ranging from 5 to 7 inches (length—top to bottom) and by 3 to 5 inches (wide), and may range in thickness from about 0.25 to 0.5 inches. Various other sizes for support members are contemplated, such as to match pediatric measurements, which may have a length lower than 5 inches and/or a width lower than 3 inches, and/or a thickness of less than 0.25 inches. Likewise, depending on the size of the wearer, or the joint area to be supported, support members may be configured with a length greater than 7 inches, and a width greater than 5 inches.

In one embodiment, a joint support apparatus may be configured using one or more support members, wherein the support members are of equal dimensions, or alternatively, wherein one of the support members are of a different size (length and/or width) and/or thickness.

The support members may be of varying shapes and sizes and may be configured with a contoured shape, such as forming a concave cavity on the joint-facing surface of the support member. In one embodiment, one support member is designed to cover a tibia side of the ankle of the wearer. In another embodiment, one support member is designed to cover a fibular side of the ankle of the wearer. In yet another embodiment, the joint support configured as an ankle support comprises one of a tibia support member or fibular support member.

In one embodiment, support members are configured with a detachable decorative attachment on the outer facing side of the support member. Decorative attachment may be of various forms, and made of various materials. In one embodiment, decorative attachment is a decorative layer, such as a layer of material comprising an image or design. The decorative layer may be of varying thickness or size, and may cover all or a portion of the support member. In another embodiment, the decorative layer may be permanently affixed to the support member, or may reversibly attached by engagement or disengagement of attachment means on the support member and decorative layer. Attachment means include snaps, buttons, magnetic fasteners, Velcro, hook and eye, and the like.

In one embodiment, securements means may be comprised of one or more of the following: an elastic or other strap configured with fastening means comprising Velcro fasteners, hook and eye closures, snaps, zippers, laces, adhesives such as tape, and any other suitable means of securing the strap in position on the assembled joint apparatus. In one embodiment, the strap is of a length ranging in inches from 11 inches to 13 inches, although the length of the strap depends on the wearer. In one embodiment, for pediatric users a shorter strap may be desired, whereas for a larger adult a longer strap may be desired. In another embodiment, the strap is of a width ranging in inches from 0.25 inches to 1.5 inches.

In one embodiment, temperature control members are configured for releasing heat or absorbing heat. In one embodiment, the temperature-control members may be one or more of a heating insert, such as inserts containing heat-releasing materials, or a cooling insert, such as an ice pack, or gel pack containing cooling materials, or other suitable heating and/or cooling agents.

In one embodiment, the support members are configured with inner compartments for holding and securing the inserts, such as pockets on the ankle-facing surface of the support. In another embodiment, the temperature-control members are reversibly attached to the ankle facing surface of the support by attachment means, such as snaps, zippers, Velcro, adhesives such as tape, or other suitable means of reversibly attaching the temperature control members to the support. In one embodiment, the temperature-control members are single-use, although in another embodiment, the temperature are reusable.

In one embodiment, first securement means is configured as a strap with a woven configuration with the support members for the purpose of maintaining compression securement. In one embodiment, first securement means is configured as an under-weave assembly positioned near the top of support members. In another embodiment, the second securement means is configured as an over-weave assembly positioned lower on the support members. The arrangement of securement means as an under-weave and/or over-weave are for convenience as well as utility. The under-weave and/or over-weave arrangement of the securement means with the support members provides for greater compression efficiency, yet still provides ease of use for the wearer. In one embodiment, second securement means is configured (in the assembled position) along the outer surface (over-weave) of the support members, for maximum control over compression of the support members against the joint area, and for comfort precision and adjustment.

In another embodiment, the inter-laced pattern of first securement means with one or more support members is dependent, in part, by the number of openings positioned on the support member. In one embodiment, a support member is configured with one or more, preferably from two (2) up to four (4) openings per support member, with the openings configured as vertical slants or openings positioned linearly (in a row) along the upper portion of the support member. The openings are of a dimension commensurate with the width and thickness of the first securement means (strap). In another embodiment, one or more vertical openings may also be positioned linearly along the lower portion of a support member, for interlacing of the second securement means.

In one embodiment, the device (joint support apparatus) may be used in combination with an ice-pack, such as a bag of ice or a cool gel pack, by placing the ice-pack or other heat/cold treatment in the space between the support member and the joint area of the wearer. The securement means are adjustable so that depending on the amount of ice needed to effectively treat an affected area of the joint is held in position by at least a portion of the support member, with a portion of the ice pack or cool gel pack abutting the joint facing side of at least one of the support members.

It will be clear to a person skilled in the art that features described in relation to any of the embodiments described above can be applicable interchangeably between the different embodiments. The embodiments described above are examples to illustrate various features of the invention, and they are not exhaustive or exclusive.

Throughout the description and claims of this specification, the words "comprise" and "contain" and variations of them mean "including but not limited to", and they are not intended to (and do not) exclude other additives, components, materials or steps. Throughout, the singular encompasses the plural unless the context otherwise requires. In particular, where the indefinite article is used, the specification is to be understood as contemplating plurality as well as singularity, unless the context requires otherwise.

Features, materials, characteristics, described in conjunction with a particular aspect, embodiment or example of the invention are to be understood to be applicable to any other aspect, embodiment or example described herein unless incompatible therewith. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. An apparatus comprising at least one flexible compression member and a first and second securement means, the apparatus configured for providing simultaneous compression to an ankle tibia, fibula and Achilles tendon of a wearer, the at least one flexible compression member having a contoured shape comprising a permanent concavity on a joint-facing side and the first and second securement means each comprising at least one strap and at least one of the group consisting of buttons, magnetic fasteners, hook and eye closures, snaps, zippers, laces, buckles and adhesives, wherein the permanent concavity on the joint-facing side is configured to at least partially surround the ankle, Achilles tendon, tibia and fibula of the wearer without restricting any motion thereof when secured therearound by the first and second securement means, wherein the ends of the first securement means are secured to each other in an underweave arrangement and the second securement means is wrapped around an outward facing side of the at least one flexible compression member below the first securement means, the ends of the second securement means being secured to each other.

2. The apparatus of claim 1, wherein the at least one flexible compression member is two flexible compression members.

3. The joint support apparatus of claim 1, wherein the at least one strap of the first and second securement means is adjustable in length.

4. The apparatus of claim 3, wherein adjustment of the at least one strap of the first and second securement means allows the apparatus to be secured simultaneously around clothing of the wearer, a temperature control member or both in addition to the ankle, tibia, fibula and Achilles tendon of the wearer.

5. The apparatus of claim 1, further comprising at least one temperature control member selected from the group consisting of heating elements and cooling elements, the temperature control member positioned within the concavity on the joint-facing side.

6. The apparatus of claim 5, wherein the concavity on the joint-facing side further comprises at least one pocket wherein the at least one temperature control member is placed.

7. The apparatus of claim 1, wherein the outward facing side of the at least one flexible compression member comprises at least one decorative feature affixed thereto.

* * * * *